US011598671B2

(12) United States Patent
Price et al.

(10) Patent No.: US 11,598,671 B2
(45) Date of Patent: Mar. 7, 2023

(54) BODY TEMPERATURE ESTIMATION VIA THERMAL INTENSITY DISTRIBUTION

(71) Applicant: Microsoft Technology Licensing, LLC, Redmond, WA (US)

(72) Inventors: Raymond Kirk Price, Redmond, WA (US); Michael Bleyer, Seattle, WA (US); Christopher Douglas Edmonds, Carnation, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 339 days.

(21) Appl. No.: 16/904,438

(22) Filed: Jun. 17, 2020

(65) Prior Publication Data

US 2021/0396583 A1 Dec. 23, 2021

(51) Int. Cl.
*G01J 5/00* (2022.01)
*G01S 17/894* (2020.01)
*G01S 17/08* (2006.01)
*G01J 5/48* (2022.01)
*G01J 5/80* (2022.01)

(52) U.S. Cl.
CPC .............. *G01J 5/0025* (2013.01); *G01S 17/08* (2013.01); *G01S 17/894* (2020.01); *G01J 5/485* (2022.01); *G01J 5/80* (2022.01); *G01J 2005/0077* (2013.01)

(58) Field of Classification Search
None
See application file for complete search history.

(56) References Cited

U.S. PATENT DOCUMENTS 5,555,512 A * 9/1996 Imai ..................... G08B 13/194
250/342
10,719,170 B2 * 7/2020 Kurz ...................... G06F 3/017
(Continued)

FOREIGN PATENT DOCUMENTS

CN 111223225 A 6/2020
WO 2018188147 A1 10/2018

OTHER PUBLICATIONS

Mendenhall, et al., "Human Skin Detection in the Visible and Near Infrared", in Journal of Applied Optics, vol. 54, Issue 35, Dec. 10, 2015, pp. 10559-10570.
(Continued)

*Primary Examiner* — Chikaodili E Anyikire
(74) *Attorney, Agent, or Firm* — Alleman Hall Creasman & Tuttle LLP (57) ABSTRACT

A method for estimating human body temperature includes receiving, via a thermal camera, one or more thermal images captured of a real-world environment, the one or more thermal images including thermal intensity values for each of a plurality of pixels. Positions of a plurality of human faces are identified in the one or more thermal images. A distribution of thermal intensity values of the plurality of human faces is determined. A position of a test human face of a test human subject is identified within a subsequent thermal image. One or more test thermal intensity values of one or more pixels corresponding to the test human face are identified. An indication of a body temperature of the test human subject is reported based on a comparison of the one or more test thermal intensity values and the distribution of thermal intensity values of the plurality of human faces.

18 Claims, 8 Drawing Sheets

(56) References Cited

U.S. PATENT DOCUMENTS

| | | | | |
|---|---|---|---|---|
| 2008/0023002 | A1* | 1/2008 | Guelzow | A62B 18/08 |
| | | | | 2/5 |
| 2009/0326381 | A1* | 12/2009 | Yuan | A61B 5/015 |
| | | | | 600/473 |
| 2015/0204556 | A1* | 7/2015 | Kusukame | F24F 11/30 |
| | | | | 250/338.3 |
| 2019/0154509 | A1* | 5/2019 | Koch | G01K 13/223 |
| 2019/0362133 | A1* | 11/2019 | Margolin | G06V 40/174 |
| 2020/0293788 | A1* | 9/2020 | Liang | H04N 5/2253 |
| 2020/0380244 | A1* | 12/2020 | Zhou | G06V 10/143 |
| 2020/0394387 | A1* | 12/2020 | Chen | A61B 5/742 |
| 2021/0338148 | A1* | 11/2021 | Marine | A61B 5/4528 |
| 2021/0404877 | A1* | 12/2021 | Lee | G06V 10/25 |
| 2022/0047160 | A1* | 2/2022 | Yoo | G16H 50/70 |

OTHER PUBLICATIONS

"International Search Report and Written Opinion Issued in PCT Application No. PCT/US21/026084", dated Jul. 9, 2021, 10 Pages.

* cited by examiner

BODY TEMPERATURE ESTIMATION VIA THERMAL INTENSITY DISTRIBUTION

BACKGROUND

Relative temperatures of objects in an environment may be estimated from thermal images. Pixels of a thermal image may encode thermal intensity values that express relative amounts of thermal energy received by the thermal camera from objects in the environment.

DETAILED DESCRIPTION

Figure 1:
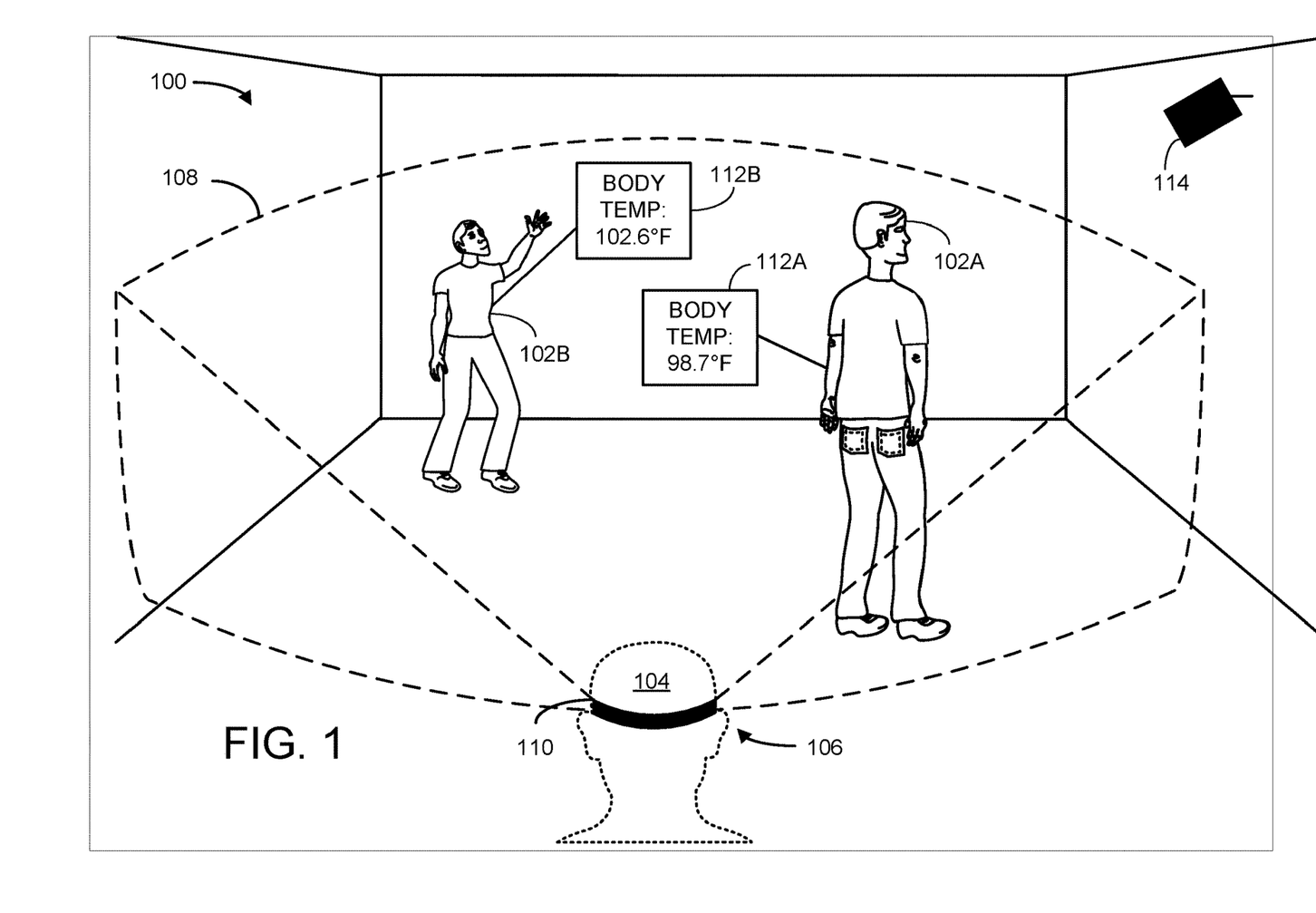
FIG. 1 schematically depicts reporting of indications of body temperatures of human subjects.

In some cases, a computing device may be used to estimate and report an indication of a body temperature of a human subject. This is schematically illustrated in FIG. 1, which shows a real-world environment 100 including two example human subjects 102A and 102B. In environment 100, a user 104 equipped with a head-mounted display device 106 has a field-of-view 108, indicating an area in which virtual content presented by a near-eye display 110 of the head-mounted display device may be visible to the user. Via the near-eye display, the head-mounted display device is displaying indications 112A and 112B of estimated body temperatures of the human subjects.

An indication of a body temperature of a human subject may take any suitable form. In the example of FIG. 1, the estimated body temperatures of the human subjects are numerically represented on the near-eye display of the head-mounted display device, such that the body temperatures are displayed at screen-space positions on the near-eye display at or near positions corresponding to the human subjects. In other examples, as will be described in more detail below, the indications of the body temperatures of the human subjects may be reported in other suitable ways (e.g., non-numerically). Furthermore, indications of human body temperatures need not be presented on near-eye displays, but rather may be presented on any suitable electronic display in any suitable manner.

The body temperatures of human subjects may be estimated in any suitable way. It will be understood that a human's internal body temperature varies across different parts of the body. Thus, for the purposes of this disclosure, the "body temperature" of a human subject will refer to the subject's core body temperature, which is often used for the purposes of medical diagnosis. This may differ from the body temperature estimated based on thermal intensity values corresponding to a subject's skin. Thus, for the purposes of this disclosure, outputting an estimated body temperature may in some cases include correcting a skin-based body temperature estimate to give a core body temperature—e.g., by adding 0.5-1.0° F. to the skin-based temperature estimate.

In some examples, a thermal image of the real-world environment may be captured by a thermal camera, the thermal image having thermal intensity values for each of a plurality of pixels of the thermal image, including pixels corresponding to human subjects that may be in the environment. The thermal camera may in some cases be integrated into a head-mounted display device (or other computing device configured to perform functions described herein), or may alternatively be a standalone camera or a component of a separate camera system, such as camera system 114. The thermal intensity values of the thermal image encode the amount of thermal energy emitted by the objects in the real-world environment and received by the thermal camera. In this manner, the relative temperatures of the objects in the real-world environment may be estimated based on their corresponding thermal intensity values in the thermal image.

However, as noted above, the thermal intensity values of the thermal image encode the relative temperatures of objects in the environment, rather than absolute temperatures (e.g., expressed in ° F. or ° C.). Furthermore, the performance of a thermal camera is often affected by a number of factors, including temperature. Thus, it can be difficult or impossible to correlate any particular thermal intensity value with a temperature value without an independent reference. In some cases, a blackbody radiator having a known temperature and thermal emissivity may be used as a reference, and human body temperatures may be estimated via a comparison of thermal intensity values of human subjects to thermal intensity values for the blackbody radiator. However, this can limit the scenarios in which the body temperature of a human subject can be estimated, as a reference blackbody radiator may not always be available.

Accordingly, the present disclosure is directed to techniques for estimating human body temperature based a distribution of thermal intensity values of a plurality of other human subjects. Specifically, the faces of a plurality of different human subjects may be identified in one or more different thermal images, and a distribution of thermal intensity values of the plurality of faces may be determined. When a test human subject is imaged in a subsequent thermal image, an indication of a body temperature of the test human subject may be reported based on a comparison of test thermal intensity values of the test human subject to the thermal intensity distribution of the plurality of faces. In this manner, the body temperatures of human subjects may be more accurately estimated, even in cases where no independent reference (e.g., blackbody radiator) is available for the thermal camera.

Figure 2:
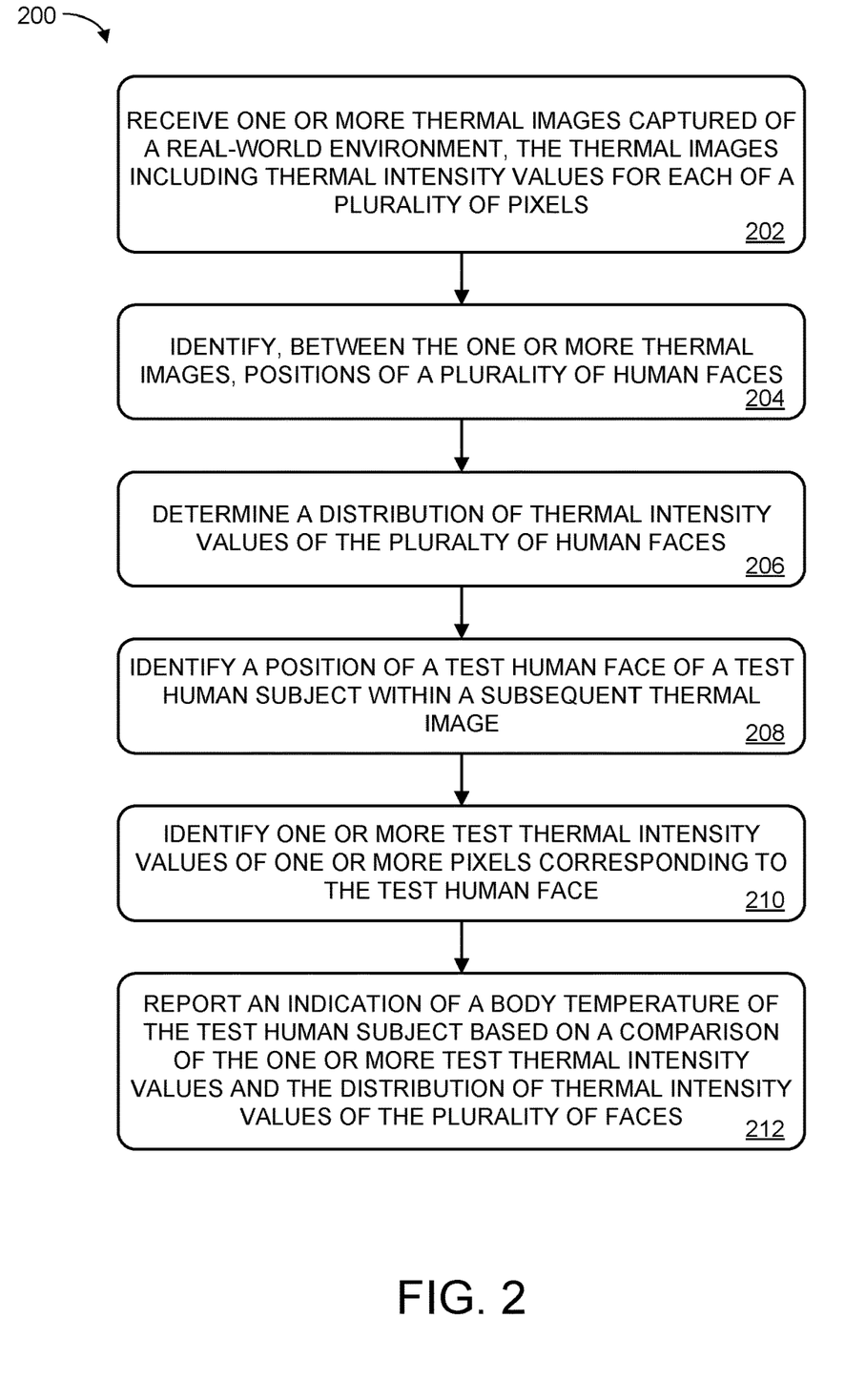
FIG. 2 illustrates an example method for estimating human body temperature.

FIG. 2 illustrates an example method 200 for estimating body temperature. Method 200 may be implemented on any suitable computing system, having any suitable form factor and hardware configuration. Steps of method 200 may be distributed between any number of different computing devices. As examples, computing devices used to implement method 200 may include desktop computers, laptop computers, servers, smartphones, tablets, augmented/virtual/mixed reality devices, wearable devices (e.g., fitness watches), media centers, vehicle computer systems, dedicated camera/monitoring systems, etc. In some examples, method 200 may be implemented via computing system 900 described below with respect to FIG. 9.

Furthermore, method 200 is primarily described with respect to reporting an indication of the body temperature of a single human subject (i.e., a "test" human subject). However, it will be understood that steps of method 200 may be performed for any number of human subjects, who may be distributed in any number of different thermal images. In other words, each of the steps of method 200 may be performed for two or more human subjects, either simultaneously (e.g., two or more human subjects are visible in a same thermal image) or sequentially (e.g., two different human subjects are identified in two different thermal images). Thus, body temperatures for any number of different human subjects may be estimated.

At 202, method 200 includes receiving, via a thermal camera, one or more thermal images captured of a real-world environment, the one or more thermal images including thermal intensity values for each of a plurality of pixels of the respective thermal images. As discussed above, a thermal camera may be integrated into a computing device that performs one or more steps of method 200 beyond image capture. Alternatively, the thermal camera may be a standalone camera, or a component of a separate camera system. For example, FIG. 1 schematically depicts an example camera system 114, which may include at least a thermal camera. Thus, the one or more computing devices configured to implement steps of method 200 may in some case receive thermal images (and/or other images) from remote cameras. Camera system 114 may additionally include other types of cameras utilizing any camera technology. As examples, camera system 114 may include a thermal camera, visual light camera, and/or depth camera. In some cases, camera system 114 may include processing componentry usable to implement steps of method 200.

Figure 3:
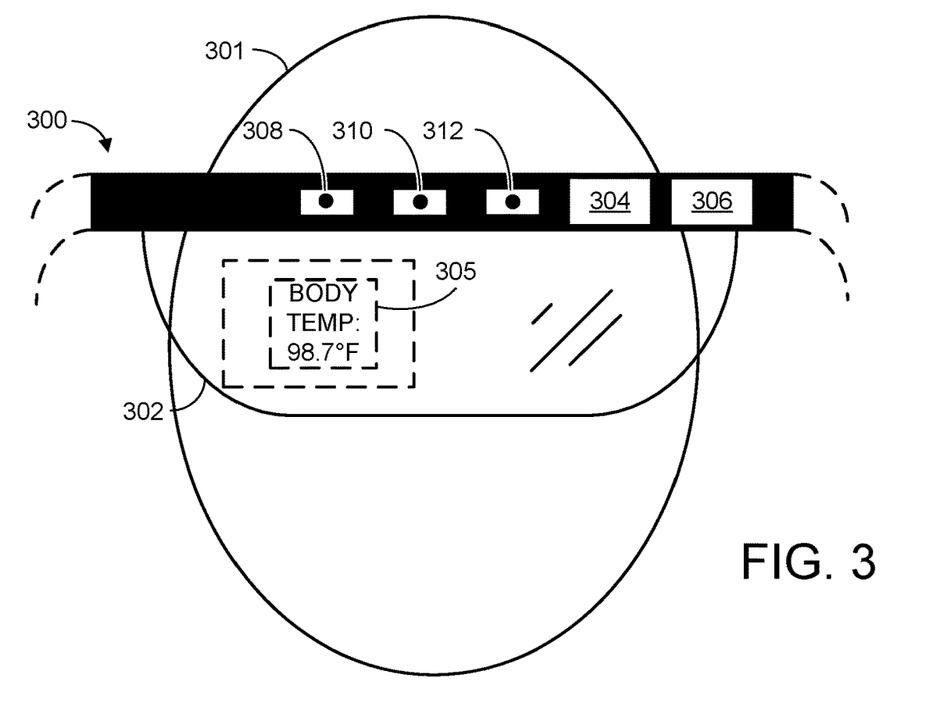
FIG. 3 schematically depicts an example head-mounted display device.

As another example, FIG. 3 schematically depicts a head-mounted display device 300 being worn on a user head 301. Head-mounted display device 300 includes a near-eye display configured to display virtual images to the user's eyes. Virtual images displayed on a near-eye display may take any suitable form, and may be provided as part of virtual and/or augmented reality experiences. In the example of FIG. 3, head-mounted display device 300 is displaying an indication 305 of an estimated body temperature of a human subject. However, as will be discussed in more detail below, indications of body temperature may take any suitable form and may be displayed via any suitable electronic display.

Head-mounted display device 300 includes a storage machine 304 that may hold instructions executable by a logic machine 306 to perform one or more steps of method 200, and/or any other suitable computer functions. Additional details with respect to the storage machine and logic machine are described below with respect to FIG. 9.

Head-mounted display device 300 also includes several cameras 308, 310, and 312. In one example, camera 308 may be a thermal camera, while camera 310 is a visible light camera and camera 312 is a depth camera. However, computing devices described herein may include any suitable collection of cameras useable to image environments and estimate body temperatures of human subjects. Each of these cameras may use any suitable technology.

In general, a "thermal camera" may include any imaging system configured to receive and encode thermal energy (e.g., infrared light) from objects in an environment. The thermal camera may typically be sensitive to light in the 8-14 µm range, and detect blackbody radiation emitted by objects in an environment. The amount of radiation emitted by each object may be dependent on the object's emissivity (or the relative power of the object to radiate heat). In some examples, a thermal camera may include a radiometric lens disposed before other optical elements of the thermal camera. Similarly, when included, visible light and depth cameras may take any suitable form. For instance, a depth camera may be a structured light depth camera or a time-of-flight depth camera. Any or all of the cameras of computing devices described herein may capture images having any suitable resolution, and the images may be captured with any suitable frame rate.

Figure 4:
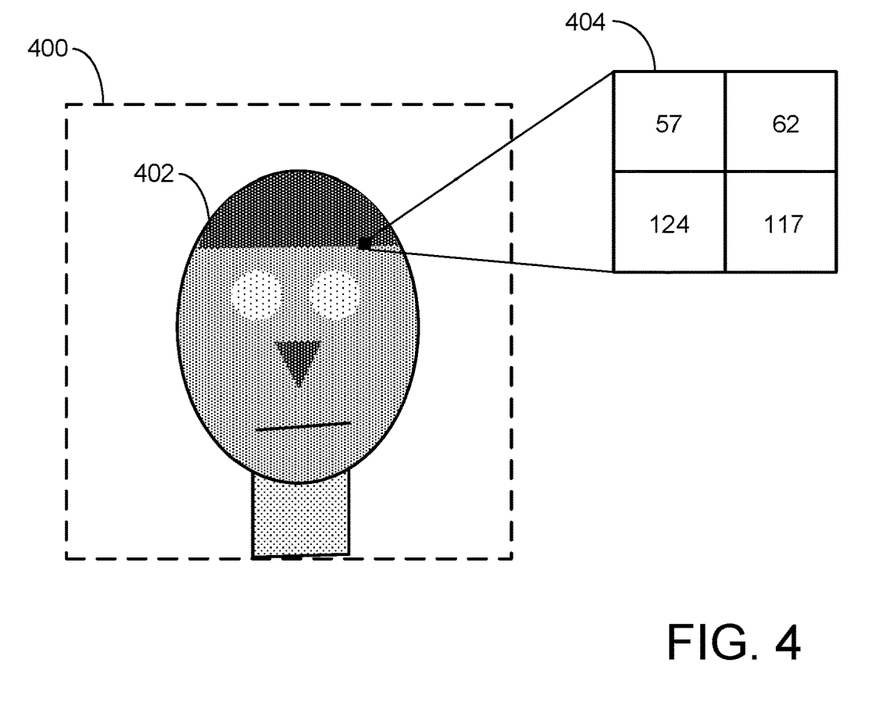
FIG. 4 schematically depicts example thermal-intensity values of a thermal image depicting a human subject.

As described herein, thermal cameras capture "thermal images" of real-world environments. One example thermal image 400 is schematically shown in FIG. 4. Thermal image 400 depicts an example human subject 402. Specifically, thermal image 400 includes a plurality of thermal intensity values 404, which correspond to four individual pixels of the thermal image. It will be understood that the thermal image may include any suitable number of pixels, and each pixel may have a corresponding thermal-intensity value.

In some cases, relatively higher thermal intensity values may correspond to regions in the imaged scene that are emitting relatively more thermal energy. In FIG. 4, pixels of thermal image 400 having relatively higher thermal intensity values are represented with relatively lighter shading. Thus, as can be seen, the face of human subject 402 is not emitting thermal energy uniformly. Rather, human faces typically exhibit some degree of temperature variation—e.g., the regions around a human's eyes are often higher temperature than regions corresponding to the human's nose, hair, ears, etc. This is reflected in FIG. 4, as relatively higher-temperature portions of the human's face have relatively higher thermal-intensity values in the thermal image.

A thermal image may take the form of any suitable data structure that includes a plurality of thermal intensity values, which in turn encode thermal energy received by the thermal camera from objects in an environment. In some cases, thermal intensity values may take the form of grey-level counts, which may have any suitable value. For example, grey-level counts may be expressed as a range between 0 and 255, or a different suitable quantization may be used. The present disclosure primarily describes thermal images as having a plurality of pixels. However, it will be understood that a "thermal image" need not be displayed on an electronic display, or otherwise visually represented in any manner. Rather, a thermal image including a plurality of pixels may in some cases be a purely non-visual data structure. Alternatively, and as will be described in more detail below, some representation of a thermal image may in some cases be visually displayed for review by a human user.

Returning to FIG. 2, at 204, method 200 includes identifying, in the one or more thermal images, positions of a plurality of human faces. Each of the plurality of human faces correspond to one or more pixels of the one or more thermal images and have corresponding thermal intensity values. In some cases, the positions of the human faces may be identified after receiving, via a second camera sensitive to a different spectrum of light than the thermal camera (e.g., camera 310 of head-mounted display device 300), one or more second images captured of the real-world environment. For example, the second camera may be visible light camera, while the second image is a visible light image. The device may then determine correspondences between pixels of the second image(s) and pixels of the thermal image(s). For example, after identifying the positions of one or more human faces within the second image(s), the positions of the one or more human faces within the thermal image(s) may be identified based on the pixel-to-pixel correspondences between the second image and thermal image pairs.

Figure 5:
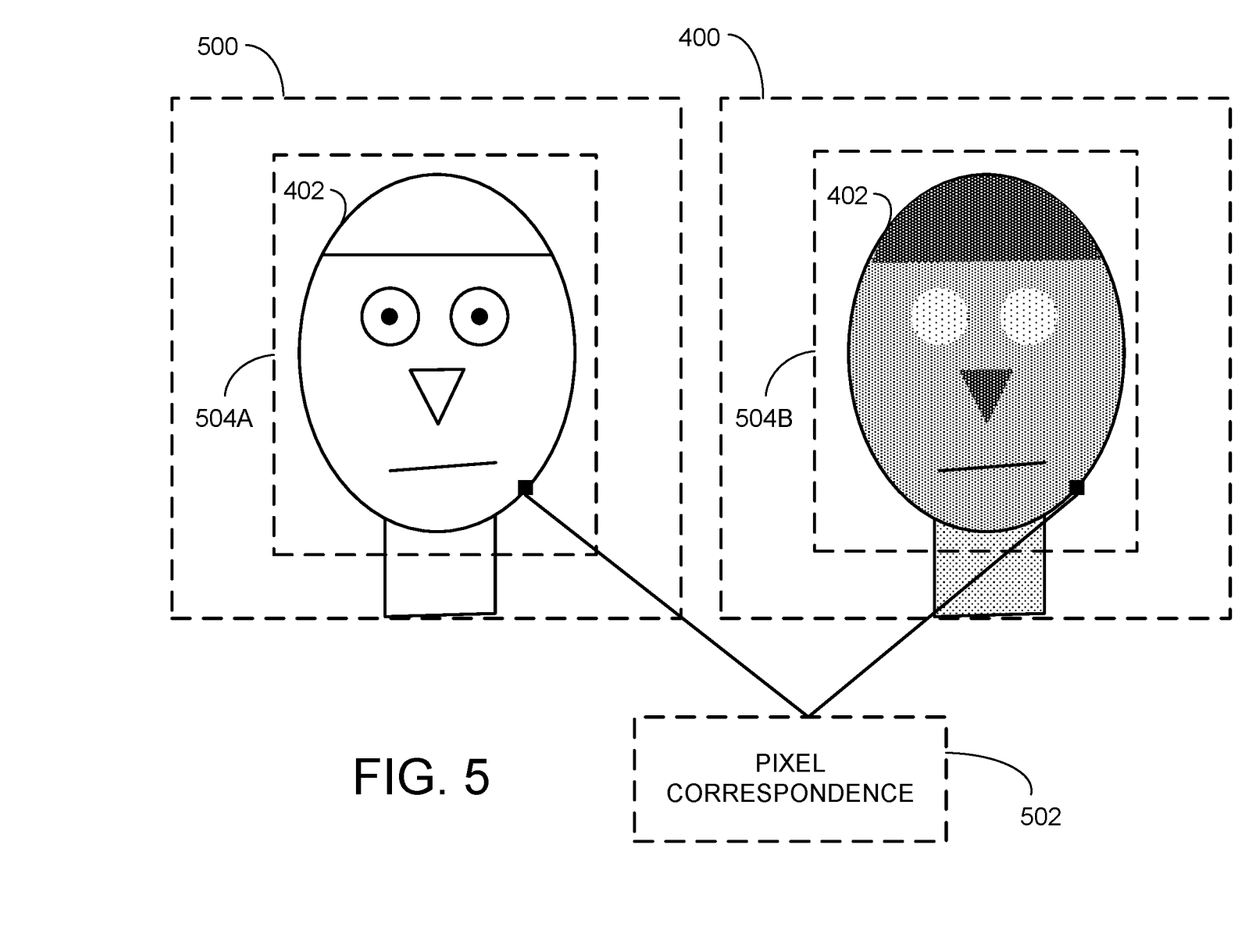
FIG. 5 schematically depicts pixel correspondences between a thermal image and a second image.

This is schematically illustrated in FIG. 5. Specifically, FIG. 5 again includes thermal image 400 depicting a single human subject 402. It will be understood that, while thermal image 400 only includes a single human subject, this is non-limiting. Rather, thermal images may include any number of human subjects. Furthermore, any number of different human subjects may be identified in any number of different thermal images.

FIG. 5 also includes a second image 500, also depicting human subject 402. The computing device identifies a plurality of pixel-to-pixel correspondences 502 between image 500 and image 400. Such correspondences may be identified in any suitable way. The second image and thermal image may be captured by different cameras (e.g., cameras 308 and 310) having different positions and perspectives. When the relative positions and perspectives of the two cameras are known, pixels of images captured by each camera may be projected into a common frame of reference—e.g., relative to a virtual camera. In this manner, it may be determined which pixels of one image (e.g., image 500) correspond to the same real-world features as the other image (e.g., image 400). Thus, when a position 504A of a face of human subject 402 in image 500 is identified, the computing device may determine which pixels of image 400 correspond to the same position 504B of the face within the thermal image. This may be repeated for any number of pairs of second and thermal images, each depicting any number of human subjects. In this manner, the positions of a plurality of human faces may be identified in one or more thermal images. In other examples, however, the positions of one or more human faces within one or more thermal images may be identified in other suitable ways.

The face of any particular human subject may be identified in any particular image in any suitable way. In some examples, any suitable facial recognition algorithm or technique may be used. For instance, one approach may include using a machine-learning trained classifier to identify pixels in an image (e.g., a visible light or thermal image) predicted to correspond to a human face.

Returning to FIG. 2, at 206, method 200 includes determining a distribution of thermal intensity values of the plurality of human faces. This is schematically illustrated with respect to FIG. 6, which shows another example thermal image 600. This thermal image includes a plurality of different human subjects 602A-602D. In this example, each of the human subjects are illustrated as if they have a uniform thermal intensity. It will be understood that this is done only for the sake of visual clarity, and that in practical scenarios, each human subject will have variable thermal intensity values across their body, as is the case for other thermal images described herein.

Figure 6:
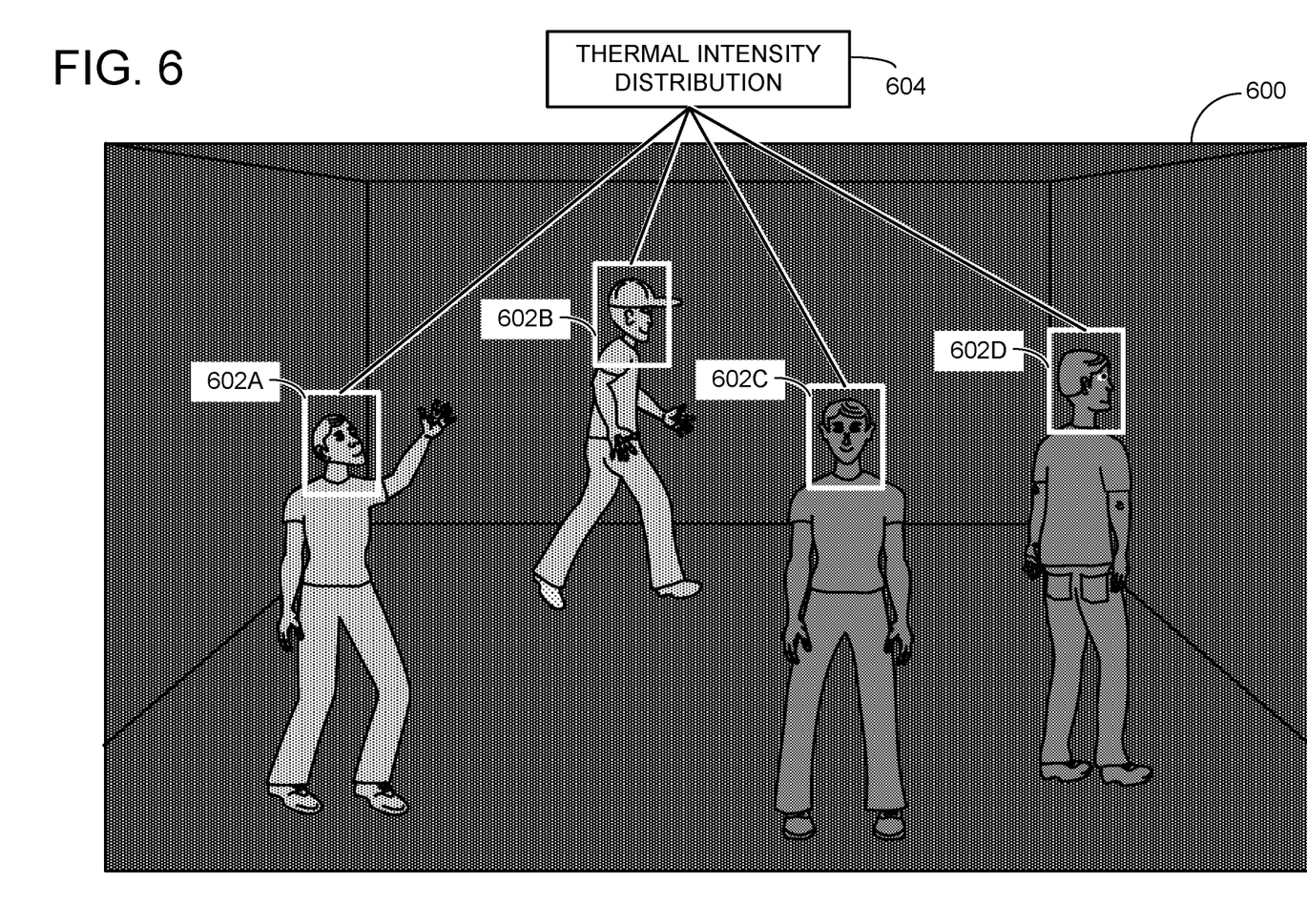
FIG. 6 schematically illustrates a thermal image including a plurality of human subjects.

In FIG. 6, the positions of the faces of the human subjects are identified, and thermal intensity values corresponding to the human faces are used to determine a thermal intensity distribution 604. In some cases, the thermal intensity values included in the thermal intensity distribution may correspond to the highest-intensity pixels for each subject. This may often correspond to the eyes, or regions around the eyes, of each human subject. Alternatively, any other suitable portion of each human subject may be used when a distribution of thermal intensity values. The positions of the faces of each human subject may be identified in any suitable way—e.g., via comparison to one or more second images as discussed above.

In the example of FIG. 6, each of the plurality of human subjects are visible in a same thermal image 600. It will be understood that this is not limiting. Rather, in other examples, each of a plurality of human subjects used to determine a thermal intensity distribution may be identified in different thermal images. Furthermore, using a thermal intensity distribution as a reference in this manner is based on the assumption that most (if not all) of the human subjects have a normal body temperature (e.g., approximately 98.6° F.). Accordingly, if any human subjects are identified as having significantly higher or lower thermal intensity than other human subjects of the plurality, they may in some cases be excluded from the thermal intensity distribution as outliers. Once the thermal intensity distribution is determined, it may be presumed that the average thermal intensity within the distribution corresponds to an average body temperature. Thus, any future thermal intensity values for a test human subject that are significantly higher than the average may be indicate a fever.

In FIG. 6, each of the plurality of human subjects are disposed at different differences away from the thermal camera. As discussed in more detail below, thermal intensity values corresponding to each human subject may undergo distance correction. Alternatively, for the purposes of determining a thermal intensity distribution, the computing device may only consider human subjects having a predetermined distance from the thermal camera (e.g., 2 meters). Similarly, as will be described in more detail below, one or more human subjects of the plurality may have different skin tones. Thus, the thermal intensity values of the plurality of human subjects may in some cases be tone-corrected prior to determining the distribution of thermal intensity values.

Returning to FIG. 2, at 208, method 200 includes identifying a position of a test human face of a test human subject within a subsequent thermal image. At 210, method 200 includes identifying one or more test thermal intensity values of one or more pixels corresponding to the test human face. Each of these steps may be done substantially as described above with respect to FIGS. 4 and 5. Notably, the thermal camera used to capture the subsequent thermal image depicting the test human subject need not be the same as the thermal camera used to capture the one or more thermal images in which the one or more human subject are identified. A "test" human subject refers to any human subject in a thermal image, for whom an indication of an estimated body temperature is to be reported. Typically, the test human subject will be identified after the thermal intensity distribution of a plurality of other human subjects is determined, as discussed above with respect to FIG. 6.

Continuing with FIG. 2, at 212, method 200 includes reporting an indication of a body temperature of the test human subject based on a comparison of the one or more test thermal intensity values and the distribution of thermal intensity values of the plurality of human faces. This is schematically illustrated with respect to FIG. 7.

Figure 7:
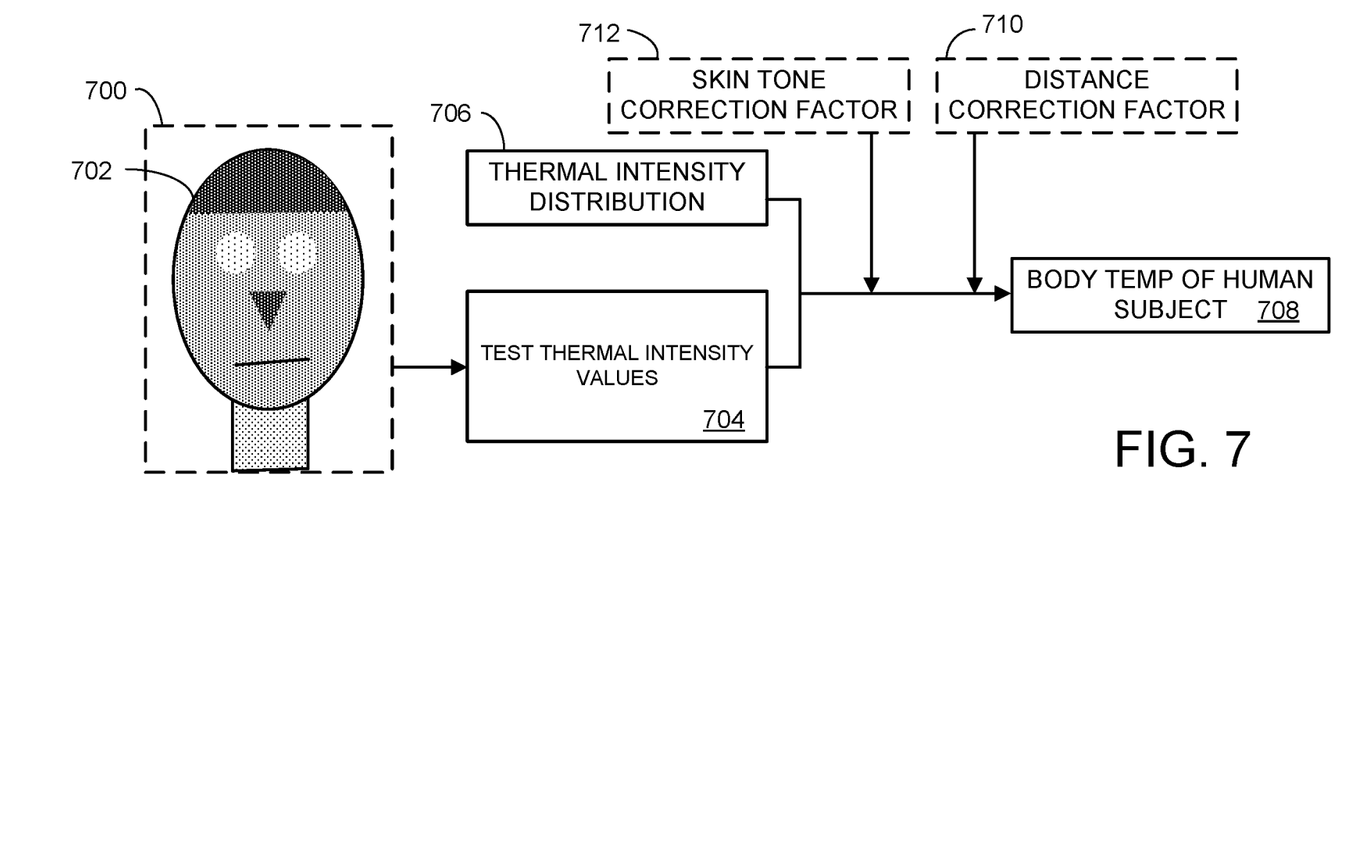
FIG. 7 schematically illustrates estimation of a body temperature of a test human subject.

Specifically, FIG. 7 shows an example thermal image 700 of a face of a test human subject 702. The computing device identifies one or more test thermal intensity values 704 of one or more pixels corresponding to the test human face. In some cases, the one or more thermal intensity values to which the distance correction factor is applied may correspond to one or more highest-intensity pixels depicting the human face. In many cases, these pixels may correspond to the skin around the human subject's eyes, and/or the eyes themselves, as is shown in FIG. 7. In other examples, however, other thermal intensity values identified as corresponding to any part of a human subject may be used to estimate body temperature.

Continuing with FIG. 7, the test thermal intensity values 704 are compared to a thermal intensity distribution 706, which may be determined from a plurality of human faces as discussed above. Based on this comparison, the computing device outputs an estimated body temperature 708 of the test human subject. This may be done in any suitable way.

In one example, as discussed above, the average thermal intensity within the thermal intensity distribution may be presumed to correspond to an average human body temperature—e.g., 98.6° F. Some indication of the body temperature of the test human subject may be determined by comparing the test thermal intensity values of the test human subject to the average thermal intensity. If the test thermal intensity values are within a threshold similarity (e.g., one standard deviation) of the average thermal intensity, the body temperature of the test human subject may be presumed to be approximately normal. By contrast, if the test thermal intensity values are significantly higher than the average thermal intensity (e.g., two or more standard deviations), it may be determined that the test human subject likely has a fever, and this may be reported as an indication of the body temperature of the test human subject.

Additionally, or alternatively, the computing device may estimate an absolute, numerical body temperature of the test human subject. For example, in some scenarios, the thermal camera may have a known sensitivity, which may be expressed in terms of a known thermal intensity change that corresponds to a known temperature change. For example, it may be known that a difference of 30 grey-level counts corresponds to a 2° F. difference in temperature. Thus, by assuming that the average thermal intensity corresponds to an average body temperature of 98.6° F., the known sensitivity of the thermal camera may be used to determine the temperature difference between the test human subject and the average body temperature, based on the difference between the test thermal intensity values and the average thermal intensity within the thermal intensity distribution.

In FIG. 7, reporting the indication of the body temperature of the human subject may optionally include applying a distance correction factor 710 to give distance-corrected thermal intensity values. When the distance between a human subject and a thermal camera increases, the human subject may appear to have a lower thermal intensity in a thermal image captured by the camera. This may be due to the fact that the thermal camera receives less thermal energy, or because relatively fewer pixels are encoding larger portions of the human, and thus high-intensity regions are averaged with lower intensity regions. For example, human subjects 102A and 102B in FIG. 1 are at different distances away from the camera. Thus, subject 102B may appear to have less thermal intensity in a thermal image than subject 102A, even when both subjects have the same core body temperature. In some cases, the body temperature of the test human subject may be estimated when the test human subject has a known, predetermined distance away from the thermal camera (e.g., 2 meters) Alternatively, in order to more accurately estimate the body temperature of a human subject, in some cases the human subject's distance away from the thermal camera may first be determined.

The distance between a human subject and a thermal camera may be determined in any suitable way. In some examples, this distance may be determined based on depth information collected by a depth camera—e.g., camera 312 of head-mounted display device 300 of FIG. 3. The depth camera may take any suitable form, including a time-of-flight depth camera and a structured light depth camera. In other examples, however, the distance between a thermal camera and a human subject may be determined without the benefit of a depth camera. For instance, a stereoscopic pair of visible light cameras may be used. When two or more subjects are present, the relative distances of each human subject may be estimated by comparing the relative sizes of each subject's head. Alternatively, a single visible light camera may be used, in tandem with a machine-learning trained distance estimation algorithm. As another example, the distance between a thermal camera and a human subject may be manually specified by a human user.

Based on this distance, a distance correction factor may be applied to the one or more test thermal intensity values to give distance-corrected thermal intensity values, and the indication of the body temperature of the test human subject may further be reported based on the distance-corrected thermal intensity values. A "distance correction factor" may take any suitable form. Typically, applying a distance correction factor will include scaling thermal intensity values either up or down by some amount that depends on the distance between the human subject and the thermal camera. For example, when human subjects are relatively far from the thermal camera, thermal intensity values corresponding to the face of the human subject may be scaled up, such that they are more consistent with a human subject who is relatively closer to the thermal camera. Alternatively, thermal intensity values corresponding to human subjects that are relatively close to the thermal camera may be scaled down such that they are more consistent with human subjects who are relatively further from the thermal camera.

The specific distance correction factor applied may be determined in any suitable way. In some cases, the distance correction factor may be determined during factory calibration of a thermal camera. For instance, during calibration, a reference object having a known temperature may be imaged at multiple different distances away from the camera. Because the temperature of the reference object is known, any changes in the thermal intensity values corresponding to the object will likely be due to distance-dependent attenuation. Based on this calibration, the computing device may determine a scaling factor that may be applied to thermal intensity values of an object at any arbitrary distance to give distance-corrected thermal intensity values, which may be equivalent to an object at a predetermined default distance—e.g., 2 meters.

Additionally, or alternatively, the distance correction factor may be determined via user calibration. In one example, the distance correction factor may be derived by determining a distance-dependent intensity change of thermal intensity values corresponding to a reference human subject, as a distance between the reference human subject and the thermal camera changes over a plurality of thermal images.

As another example, the distance correction factor may be derived based on identifying a plurality of different human subjects at different distances from the thermal camera in a plurality of different thermal images, and determining a distance-dependent intensity distribution of thermal intensity values corresponding to the plurality of different human subjects.

Additionally, or alternatively, a skin tone correction factor 712 may be applied to the test thermal intensity values when reporting an indication of the body temperature of the test human subject. This may give a set of tone-corrected thermal intensity values, and the indication of the body temperature of the test human subject may further be reported based on these tone-corrected thermal intensity values. For example, the thermal emissivity value of light-colored human skin has been estimated to be approximately 0.95, while the thermal emissivity of dark-colored skin is approximately 0.98. Thus, for a given body temperature, darker-skinned human subjects may have relatively higher thermal intensity values in a thermal image than lighter-skinned human subjects. It may therefore in some cases be beneficial to first identify the skin tone of a human subject, then apply a skin tone correction factor to thermal-intensity values corresponding to the human subject to give tone-corrected thermal intensity values.

The skin tone of a human subject may be identified in any suitable way. In one example, the skin tone of a human subject may be identified based on the color of a human face in a second image, such as a visible light image. For example, returning briefly to FIG. 5, the color of the face of human subject 402 may be identified based on the colors of pixels identified as corresponding to the position 504A of the human face within image 500. Additionally, or alternatively, the skin tone of a human subject may be identified from images that use non-visible wavelengths, such as images captured by a depth camera. As another example, the skin tone of a human subject may be manually specified by a human user.

Applying a skin tone correction factor may include scaling thermal intensity values for lighter-skinned human subjects up, such that they are more consistent with darker-skinned human subjects. Alternatively, thermal intensity values for darker-skinned human subjects may be scaled down, such that they are more consistent with lighter-skinned human subjects. As another example, thermal intensity values for all human subjects may be scaled up by variable amounts, to give thermal intensity values consistent with a tone-neutral thermal emissivity value—e.g., 1.0.

In some implementations, skin tone correction factors may be predetermined for different specific skin tones. For example, the computing device may maintain a lookup table or similar data structure that defines a plurality of skin tone correction factors for use with a plurality of different skin tones. Alternatively, skin tone correction factors may be dynamically calculated on-the-fly based on a specific identified skin tone of a particular human subject.

Figure 8A:
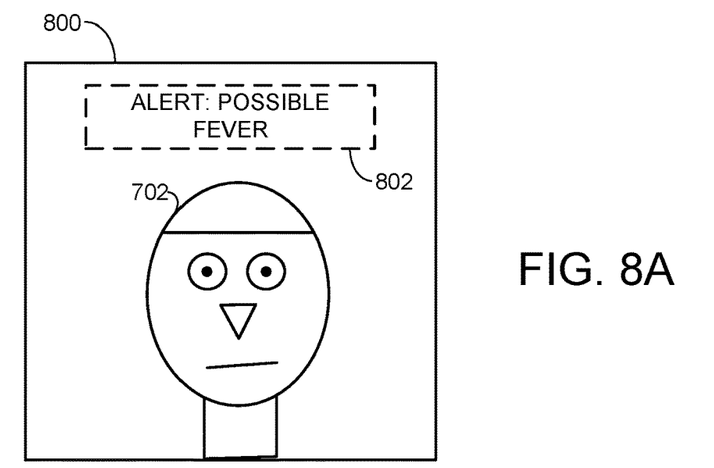
FIGS. 8A-8C schematically illustrate different example indications of a body temperature of a human subject.
Figure 8B:
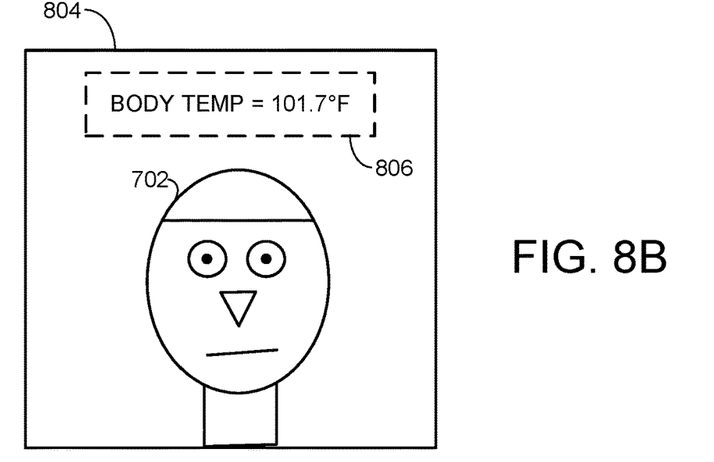
Figure 8C:
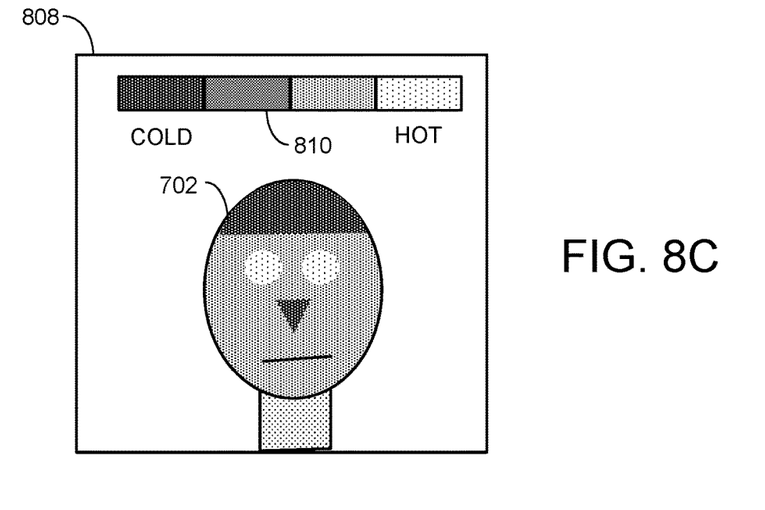

Once the body temperature of the test human subject is estimated from the test thermal intensity values, an indication of the body temperature may be reported in any suitable way. FIGS. 8A-8C schematically depict various examples of ways in which an indication of a body temperature of a test human subject may be reported. Specifically, FIG. 8A depicts an example displayed image 800, again showing test human subject 702. Displayed image 800 may, for example, be a visible light image captured by a visible light camera. Displayed image 800 also includes a notification 802 that the body temperature of the test human subject is estimated to exceed a predetermined temperature threshold—e.g., 101° F. Any suitable temperature threshold may be used. Furthermore, notification 802 is a non-limiting example. Other notifications may include any suitable information, and may take any suitable form, including non-visual forms—e.g., a different notification may be output as an audio alert.

FIG. 8B shows a different example displayed image 804, again taking the form of a visible light image depicting test human subject 702. In this example, however, the indication of the body temperature of the human subject is reported via a notification 806, which includes an absolute, numerical estimate of the human subject's body temperature. Again, notification 806 may take any suitable form and include any suitable information.

FIG. 8C shows a third example displayed image 808. In this example, the displayed image is a representation of a thermal image depicting test human subject 702. In other words, pixels of displayed image 808 are based on thermal intensity values, rather than wavelengths of visible light. In some cases, the pixel values of a representation of a thermal image, such as displayed image 808, may differ from pixel values of an original thermal image—e.g., to make the displayed image easier for human users to parse. For instance, the scale of the thermal intensity values may be changed, or artificial colors may be used to represent the thermal intensity of the various pixels.

Displayed image 808 also includes a thermal reference 810, indicating to a human user the relative temperatures that each pixel of the thermal image correspond to. While different degrees of grey-scale shading are used in this example, this is not limiting. Rather, other examples may use spectra of visible light colors—e.g., a range from blue to red. In other words, the indication of the body temperature of the test human subject may in some cases be reported via colors of pixels used to represent the test human subject in the displayed image.

It will be understood that each of displayed images 800, 804, and 808 are non-limiting. In general, a displayed image may be a visible light image, a representation of a thermal image, or take any other suitable form. Furthermore, a displayed image may represent a test human subject in any suitable way, and similarly report an estimated body temperature of the test human subject in any suitable way. Displayed images may be presented using any suitable electronic display. For example, displayed images may be presented using a near-eye display (e.g., near-eye displays 110 or 302), or any other type of electronic display, including televisions, computer monitors, mobile device displays, etc.

The methods and processes described herein may be tied to a computing system of one or more computing devices. In particular, such methods and processes may be implemented as an executable computer-application program, a network-accessible computing service, an application-programming interface (API), a library, or a combination of the above and/or other compute resources.

Figure 9:
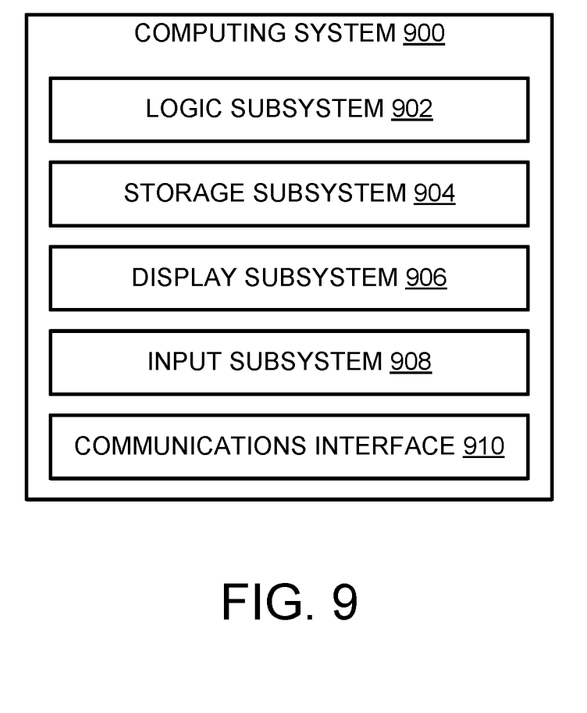
FIG. 9 schematically illustrates an example computing system.

FIG. 9 schematically shows a simplified representation of a computing system 900 configured to provide any to all of the compute functionality described herein. Computing system 900 may take the form of one or more personal computers, network-accessible server computers, tablet computers, home-entertainment computers, gaming devices, mobile computing devices, mobile communication devices (e.g., smart phone), virtual/augmented/mixed reality computing devices, wearable computing devices, Internet of Things (IoT) devices, embedded computing devices, and/or other computing devices.

Computing system 900 includes a logic subsystem 902 and a storage subsystem 904. Computing system 900 may optionally include a display subsystem 906, input subsystem 908, communication subsystem 910, and/or other subsystems not shown in FIG. 9.

Logic subsystem 902 includes one or more physical devices configured to execute instructions. For example, the logic subsystem may be configured to execute instructions that are part of one or more applications, services, or other logical constructs. The logic subsystem may include one or more hardware processors configured to execute software instructions. Additionally, or alternatively, the logic subsystem may include one or more hardware or firmware devices configured to execute hardware or firmware instructions. Processors of the logic subsystem may be single-core or multi-core, and the instructions executed thereon may be configured for sequential, parallel, and/or distributed processing. Individual components of the logic subsystem optionally may be distributed among two or more separate devices, which may be remotely located and/or configured for coordinated processing. Aspects of the logic subsystem may be virtualized and executed by remotely-accessible, networked computing devices configured in a cloud-computing configuration.

Storage subsystem 904 includes one or more physical devices configured to temporarily and/or permanently hold computer information such as data and instructions executable by the logic subsystem. When the storage subsystem includes two or more devices, the devices may be collocated and/or remotely located. Storage subsystem 904 may include volatile, nonvolatile, dynamic, static, read/write, read-only, random-access, sequential-access, location-addressable, file-addressable, and/or content-addressable devices. Storage subsystem 904 may include removable and/or built-in devices. When the logic subsystem executes instructions, the state of storage subsystem 904 may be transformed—e.g., to hold different data.

Aspects of logic subsystem 902 and storage subsystem 904 may be integrated together into one or more hardware-logic components. Such hardware-logic components may include program- and application-specific integrated circuits (PASIC/ASICs), program- and application-specific standard products (PSSP/ASSPs), system-on-a-chip (SOC), and complex programmable logic devices (CPLDs), for example.

The logic subsystem and the storage subsystem may cooperate to instantiate one or more logic machines. As used herein, the term "machine" is used to collectively refer to the combination of hardware, firmware, software, instructions, and/or any other components cooperating to provide computer functionality. In other words, "machines" are never abstract ideas and always have a tangible form. A machine may be instantiated by a single computing device, or a machine may include two or more sub-components instantiated by two or more different computing devices. In some implementations a machine includes a local component (e.g., software application executed by a computer processor) cooperating with a remote component (e.g., cloud computing service provided by a network of server computers). The software and/or other instructions that give a particular machine its functionality may optionally be saved as one or more unexecuted modules on one or more suitable storage devices.

When included, display subsystem 906 may be used to present a visual representation of data held by storage subsystem 904. This visual representation may take the form of a graphical user interface (GUI). Display subsystem 906 may include one or more display devices utilizing virtually any type of technology. In some implementations, display subsystem may include one or more virtual-, augmented-, or mixed reality displays.

When included, input subsystem 908 may comprise or interface with one or more input devices. An input device may include a sensor device or a user input device. Examples of user input devices include a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition.

When included, communication subsystem 910 may be configured to communicatively couple computing system 900 with one or more other computing devices. Communication subsystem 910 may include wired and/or wireless communication devices compatible with one or more different communication protocols. The communication subsystem may be configured for communication via personal-, local- and/or wide-area networks.

This disclosure is presented by way of example and with reference to the associated drawing figures. Components, process steps, and other elements that may be substantially the same in one or more of the figures are identified coordinately and are described with minimal repetition. It will be noted, however, that elements identified coordinately may also differ to some degree. It will be further noted that some figures may be schematic and not drawn to scale. The various drawing scales, aspect ratios, and numbers of components shown in the figures may be purposely distorted to make certain features or relationships easier to see.

In an example, a method for estimating human body temperature comprises: receiving, via a thermal camera, one or more thermal images captured of a real-world environment, the one or more thermal images including thermal intensity values for each of a plurality of pixels of the one or more thermal images; identifying, in the one or more thermal images, positions of a plurality of human faces, each of the plurality of human faces corresponding to one or more pixels of the one or more thermal images having corresponding thermal intensity values; determining a distribution of thermal intensity values of the plurality of human faces; identifying a position of a test human face of a test human subject within a subsequent thermal image; identifying one or more test thermal intensity values of one or more pixels corresponding to the test human face; and reporting an indication of a body temperature of the test human subject based on a comparison of the one or more test thermal intensity values and the distribution of thermal intensity values of the plurality of human faces. In this example or any other example, the indication of the body temperature of the test human subject is further reported based on a known sensitivity of the thermal camera. In this example or any other example, the thermal intensity values are grey-level counts. In this example or any other example, the test human subject is at a known predetermined distance away from the thermal camera. In this example or any other example, the method further comprises receiving an indication of a distance between the test human subject and the thermal camera, applying a distance correction factor to the one or more test thermal intensity values based on the determined distance to give distance-corrected thermal intensity values, and reporting the indication of the body temperature of the test human subject further based on the distance-corrected thermal intensity values. In this example or any other example, the indication of the distance between the test human subject and the thermal camera is received from a depth camera. In this example or any other example, the method further comprises identifying a skin tone of the test human subject, applying a skin tone correction factor to the one or more test thermal intensity values to give tone-corrected thermal intensity values, and further reporting the indication of the body temperature of the test human subject based on the tone-corrected thermal intensity values. In this example or any other example, the method further comprises receiving, via a second camera sensitive to a different spectrum of light from the thermal camera, a second image captured of the real-world environment, identifying a position of the test human face within the second image, and identifying the position of the test human face within the subsequent thermal image based on correspondences between the pixels of the second image and the pixels of the subsequent thermal image. In this example or any other example, the one or more pixels corresponding to the test human face, having the test thermal intensity values based on which the indication of the body temperature of the test human subject is reported, include one or more highest-intensity pixels of the test human face. In this example or any other example, reporting the indication of the body temperature of the test human subject includes estimating an absolute body temperature of the test human subject. In this example or any other example, the absolute body temperature of the test human subject is numerically represented on a near-eye display of a head-mounted display device, such that the absolute body temperature is displayed at a screen space position on the near-eye display at or near a position corresponding to the test human subject. In this example or any other example, the method further comprises displaying a representation of the subsequent thermal image on an electronic display, and reporting the indication of the body temperature of the test human subject via colors of pixels used to represent the test human subject. In this example or any other example, reporting the indication of the body temperature of the test human subject includes outputting a notification that the body temperature of the test human subject is estimated to exceed a predetermined temperature threshold.

In an example, a computing device comprises: a thermal camera; a logic machine; and a storage machine holding instructions executable by the logic machine to: receive, via the thermal camera, one or more thermal images captured of a real-world environment, the one or more thermal images including thermal intensity values for each of a plurality of pixels of the one or more thermal images; identify, in the one or more thermal images, positions of a plurality of human faces, each of the plurality of human faces corresponding to one or more pixels of the one or more thermal images having corresponding thermal intensity values; determine a distribution of thermal intensity values of the plurality of human faces; identify a position of a test human face of a test human subject within a subsequent thermal image; identify one or more test thermal intensity values of one or more pixels corresponding to the test human face; and report an indication of a body temperature of the test human subject based on a comparison of the one or more test thermal intensity values and the distribution of thermal intensity of the plurality of human faces. In this example or any other example, the thermal intensity values are grey-level counts, and where the indication of the body temperature of the test human subject is further reported based on a known sensitivity of the thermal camera. In this example or any other example, the instructions are further executable to receive an indication of a distance between the test human subject and the thermal camera, apply a distance correction factor to the one or more test thermal intensity values based on the determined distance to give distance-corrected thermal intensity values, and report the indication of the body temperature of the test human subject further based on the distance-corrected thermal intensity values. In this example or any other example, the instructions are further executable to identify a skin tone of the test human subject, apply a skin tone correction factor to the one or more test thermal intensity values to give tone-corrected thermal intensity values, and further report the indication of the body temperature of the test human subject based on the tone-corrected thermal intensity values. In this example or any other example, the one or more pixels corresponding to the test human face, having the test thermal intensity values based on which the indication of the body temperature of the test human subject is reported, include one or more highest-intensity pixels of the test human face. In this example or any other example, the instructions are further executable to display a representation of the subsequent thermal image on an electronic display, and report the indication of the body temperature of the test human subject via colors of pixels used to represent the test human subject.

In an example, a head-mounted display device comprises: a near-eye display; a thermal camera; a logic machine; and a storage machine holding instructions executable by the logic machine to: receive, via the thermal camera, one or more thermal images captured of a real-world environment, the one or more thermal images including thermal intensity values for each of a plurality of pixels of the one or more thermal images; identify, in the one or more thermal images, positions of a plurality of human faces, each of the plurality of human faces corresponding to one or more pixels of the one or more thermal images having corresponding thermal intensity values; determine a distribution of thermal intensity values of the plurality of human faces; identify a position of a test human face of a test human subject within a subsequent thermal image; identify one or more test thermal intensity values of one or more pixels corresponding to the test human face; estimate a body temperature of the test human subject based on a comparison of the one or more test thermal intensity values and the distribution of thermal intensity values of the plurality of human faces; and numerically display the body temperature of the human subject at a screen space position on the near-eye display at or near a position corresponding to the test human subject.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The invention claimed is:

1. A method for estimating human body temperature, the method comprising:
receiving, via a thermal camera, one or more thermal images captured of a real-world environment, the one or more thermal images including thermal intensity values for each of a plurality of pixels of the one or more thermal images;
identifying, in the one or more thermal images, positions of a plurality of human faces, each of the plurality of human faces corresponding to one or more pixels of the one or more thermal images having corresponding thermal intensity values;
determining a distribution of thermal intensity values of the plurality of human faces;

identifying a position of a test human face of a test human subject within a subsequent thermal image;

identifying one or more test thermal intensity values of one or more pixels corresponding to the test human face; and reporting an indication of a body temperature of the test human subject based on a comparison of the one or more test thermal intensity values and the distribution of thermal intensity values of the plurality of human faces, where the one or more pixels having the one or more test thermal intensity values based on which the indication of the body temperature of the test human subject is reported include one or more highest-intensity pixels of the test human face.

2. The method of claim 1, where the indication of the body temperature of the test human subject is further reported based on a known sensitivity of the thermal camera.

3. The method of claim 1, where the thermal intensity values are grey-level counts.

4. The method of claim 1, where the test human subject is at a known predetermined distance away from the thermal camera.

5. The method of claim 1, further comprising receiving an indication of a distance between the test human subject and the thermal camera, applying a distance correction factor to the one or more test thermal intensity values based on the determined distance to give distance-corrected thermal intensity values, and reporting the indication of the body temperature of the test human subject further based on the distance-corrected thermal intensity values.

6. The method of claim 5, where the indication of the distance between the test human subject and the thermal camera is received from a depth camera.

7. The method of claim 1, further comprising identifying a skin tone of the test human subject, applying a skin tone correction factor to the one or more test thermal intensity values to give tone-corrected thermal intensity values, and further reporting the indication of the body temperature of the test human subject based on the tone-corrected thermal intensity values.

8. The method of claim 1, further comprising receiving, via a second camera sensitive to a different spectrum of light from the thermal camera, a second image captured of the real-world environment, identifying a position of the test human face within the second image, and identifying the position of the test human face within the subsequent thermal image based on correspondences between the pixels of the second image and the pixels of the subsequent thermal image.

9. The method of claim 1, where reporting the indication of the body temperature of the test human subject includes estimating an absolute body temperature of the test human subject.

10. The method of claim 9, where the absolute body temperature of the test human subject is numerically represented on a near-eye display of a head-mounted display device, such that the absolute body temperature is displayed at a screen space position on the near-eye display at or near a position corresponding to the test human subject.

11. The method of claim 1, further comprising displaying a representation of the subsequent thermal image on an electronic display, and reporting the indication of the body temperature of the test human subject via colors of pixels used to represent the test human subject.

12. The method of claim 1, where reporting the indication of the body temperature of the test human subject includes outputting a notification that the body temperature of the test human subject is estimated to exceed a predetermined temperature threshold.

13. A computing device, comprising:
a thermal camera;
a logic machine; and
a storage machine holding instructions executable by the logic machine to:
receive, via the thermal camera, one or more thermal images captured of a real-world environment, the one or more thermal images including thermal intensity values for each of a plurality of pixels of the one or more thermal images;
identify, in the one or more thermal images, positions of a plurality of human faces, each of the plurality of human faces corresponding to one or more pixels of the one or more thermal images having corresponding thermal intensity values;
determine a distribution of thermal intensity values of the plurality of human faces;
identify a position of a test human face of a test human subject within a subsequent thermal image;
identify one or more test thermal intensity values of one or more pixels corresponding to the test human face; and
report an indication of a body temperature of the test human subject based on a comparison of the one or more test thermal intensity values and the distribution of thermal intensity of the plurality of human faces, where the one or more pixels having the one or more test thermal intensity values based on which the indication of the body temperature of the test human subject is reported include one or more highest-intensity pixels of the test human face.

14. The computing device of claim 13, where the thermal intensity values are grey-level counts, and where the indication of the body temperature of the test human subject is further reported based on a known sensitivity of the thermal camera.

15. The computing device of claim 13, where the instructions are further executable to receive an indication of a distance between the test human subject and the thermal camera, apply a distance correction factor to the one or more test thermal intensity values based on the determined distance to give distance-corrected thermal intensity values, and report the indication of the body temperature of the test human subject further based on the distance-corrected thermal intensity values.

16. The computing device of claim 13, where the instructions are further executable to identify a skin tone of the test human subject, apply a skin tone correction factor to the one or more test thermal intensity values to give tone-corrected thermal intensity values, and further report the indication of the body temperature of the test human subject based on the tone-corrected thermal intensity values.

17. The computing device of claim 13, where the instructions are further executable to display a representation of the subsequent thermal image on an electronic display, and report the indication of the body temperature of the test human subject via colors of pixels used to represent the test human subject.

18. A head-mounted display device, comprising:
a near-eye display;
a thermal camera;
a logic machine; and
a storage machine holding instructions executable by the logic machine to:

receive, via the thermal camera, one or more thermal images captured of a real-world environment, the one or more thermal images including thermal intensity values for each of a plurality of pixels of the one or more thermal images;

identify, in the one or more thermal images, positions of a plurality of human faces, each of the plurality of human faces corresponding to one or more pixels of the one or more thermal images having corresponding thermal intensity values;

determine a distribution of thermal intensity values of the plurality of human faces;

identify a position of a test human face of a test human subject within a subsequent thermal image;

identify one or more test thermal intensity values of one or more pixels corresponding to the test human face;

estimate a body temperature of the test human subject based on a comparison of the one or more test thermal intensity values and the distribution of thermal intensity values of the plurality of human faces, where the one or more pixels having the one or more test thermal intensity values based on which the body temperature of the test human subject is estimated include one or more highest-intensity pixels of the test human face; and numerically display the body temperature of the human subject at a screen space position on the near-eye display at or near a position corresponding to the test human subject.

* * * * *